United States Patent [19]

Blank

[11] Patent Number: 5,102,961

[45] Date of Patent: Apr. 7, 1992

[54] ISOCYANATE MODIFIED BLOCKED SULFONIC ACID ESTER AS A CROSSLINKING CATALYST

[75] Inventor: Werner J. Blank, Wilton, Conn.

[73] Assignee: King Industries, Norwalk, Conn.

[21] Appl. No.: 293,650

[22] Filed: Jan. 5, 1989

[51] Int. Cl.[5] .................. C08L 63/00; C07C 303/10; C08G 59/14

[52] U.S. Cl. ...................... 525/528; 525/126; 525/162; 525/163; 525/452; 525/535; 558/47; 558/49

[58] Field of Search .............. 558/47, 49; 525/528

[56] References Cited

U.S. PATENT DOCUMENTS

| | | |
|---|---|---|
| 3,842,021 | 10/1974 | Grant . |
| 3,868,338 | 2/1975 | Parsons, III . |
| 4,189,562 | 2/1980 | Dieterich .............................. 558/47 |
| 4,200,729 | 4/1980 | Calbo . |
| 4,251,665 | 2/1981 | Calbo . |
| 4,454,274 | 6/1984 | Singer et al. . |
| 4,469,832 | 9/1984 | Singer et al. . |
| 4,477,618 | 10/1984 | Singer et al. . |
| 4,504,372 | 3/1985 | Kirchmayer et al. . |
| 4,510,290 | 4/1985 | Kirchmayer et al. . |
| 4,829,105 | 5/1989 | Yamada et al. ...................... 525/528 |

FOREIGN PATENT DOCUMENTS 56-041265  4/1981  Japan .

OTHER PUBLICATIONS

Saxon et al., Curing Relations of Hexakis (methoxymethyl) melamine and Its Combinations with Acrylic Polymers, *J. Applied Polymer Science*, 8, pp. 475-488 (1964).

Cyanamid Bulletin, Catalysts for Low Temperature Cure in Solvent-Based, Amino Cross-Linked Coatings, CRT—159.

Netherlands Chemical Substances Act, Article 9.

United States Toxic Substances Act.

*Primary Examiner*—John C. Bleutge
*Assistant Examiner*—Vasu S. Jagannathan
*Attorney, Agent, or Firm*—Morgan & Finnegan

[57] ABSTRACT

The present invention is directed to a polymeric isocyanate modified epoxy blocked sulfonic acid ester as a catalyst for the crosslinking of polymers having hydroxyl, carboxyl, and amide functional groups with a crosslinking agent and resin compositions containing the same. More particularly, the present invention is directed to a polymeric isocyanate modified epoxy blocked sulfonic acid ester with a molecular weight of about 1000 preferably prepared from a sulfonic acid, an epoxy resin and a mono- or di-isocyanate and resin compositions containing the polymeric isocyanate modified epoxy blocked sulfonic acid ester catalyst. The catalyst when used in the crosslinking or curing of hydroxyl, carboxyl or amide containing polymers with an acid catalyzed amino-formaldehyde crosslinking agent, such as hexamethoxymethylmelamine ("HMMA"), produced polymeric film coatings which have superior hardness, impact resistance, adhesion, improved blister resistance, salt spray characteristics and flexibility.

9 Claims, No Drawings

ISOCYANATE MODIFIED BLOCKED SULFONIC ACID ESTER AS A CROSSLINKING CATALYST

INTRODUCTION

The present invention is directed to a polymeric isocyanate modified epoxy blocked sulfonic acid ester as a catalyst for the crosslinking of polymers having hydroxyl, carboxyl, and amide functional groups with a crosslinking agent and resin compositions containing the same. More particularly, the present invention is directed to a polymeric isocyanate modified epoxy blocked sulfonic acid ester with a molecular weight of about 1000 preferably prepared from a sulfonic acid, an epoxy resin and a mono- or di- isocyanate and resin compositions containing the polymeric isocyanate modified epoxy blocked sulfonic acid ester catalyst. The catalyst when used in the crosslinking or curing of hydroxyl, carboxyl or amide containing polymers with an acid catalyzed amino-formaldehyde crosslinking agent, such as hexamethoxymethylmelamine ("HMMA"), produced polymeric film coatings which have superior hardness, impact resistance, adhesion, improved blister resistance, salt spray characteristics and flexibility. Moreover, the catalysts themselves have improved stability and the resin compositions formulated with the catalyst are more stable and the cured resins have higher resistivity to electrical conductance.

BACKGROUND

The crosslinking of resins containing hydroxyl functional groups with amino-plast resins are known to produced good quality thermosetting plastic coatings on metal. It is also known that an acid such as p-toluenesulfonic acid can be used as a crosslinking catalyst.

Robert Saxon et al., *J. of App. Polymer Sc.*, 8, pp. 475–488 (1964), reported the use of p-toluenesulfonic acid (p-TSA) as a curing catalyst for HMMA alone or in combination with acrylic polymers. It was found that although curing can take place without the presence of an acid catalyst, the rate of cure is very slow and the curing temperature required is very high. The presence of p-TSA lowered the curing temperature and increased the cure rate. However, resin compositions containing p-TSA is unstable at room temperature and required mixing of the ingredients immediately prior to use. This makes it difficult to control the quality of the resin produced and to put together a stable one package coating system.

Grant et al., U.S. Pat. No. 3,842,021 and Parsons et al., U.S. Pat. No. 3,868,338 described epoxy blocked p-TSA as a catalyst for the curing of polyster-HMMA resins. The catalyst is prepared from p-TSA wherein the acid group is blocked with a compound containing an oxirane group, specifically a bisphenol A epichlorhydrin epoxy resin. The maximum molecular weight achievable using such a process is about 700.

Sulfonic acid blocked with other groups such as 2-hydroxy-cycloalkyl or aryl substituted 2-hydroxy cycloalkyl groups (U.S. Pat. No. 4,469,832); alpha-hydroxy carbonyl groups (U.S. Pat. No. 4,510,290); oxa-aza cyclopentanes (U.S. Pat. No. 4,200,729 and U.S. Pat. No. 4,251,665); beta-hydroxy free groups (U.S. Pat. No. 4,454,274 and U.S. Pat. No. 4,477,618) and beta-hydroxy carbonyl groups (U.S. Pat. No. 4,504,372) have been reported.

Catalysts for low temperature cure of amino crosslinked coatings can be found also in American Cyanamid Bulletin # CRT-159 (1978).

All of the blocked sulfonic acid ester catalysts described result from an equimolar reaction of the blocking group and the sulfonic acid group. Thus, none of these are polymeric and are of low molecular weight, less than about 700. Moreover, many of the blocked sulfonic acid catalysts reported are not stable and cannot be stored for long periods of time. Compounds with amino and alcohol groups have been used to improve storage stability. However, resins cured with amine blocked sulfonic acid catalysts are less impact resistant, and have poor resistivity. The resins cured with amine blocked sulfonic acid catalysts also have a tendency to wrinkle on cure and give variations in gloss. Further, coating systems containing amine blocked sulfonic acids also has low resistivity and are, therefore, difficult or cannot be used in electrostatic spray applications, which are particularly important in automotive and appliance coatings, where high transfer efficiencies are required.

Currently, many countries require toxicity testing for new compounds. In particular, under present regulatory schemes, U.S. and European countries require toxicity testing of compounds with molecular weights of less than about 1000; whereas, polymers with molecular weights of about 1000 or greater are exempt from such testing. Thus, toxicity testing would be required even for new blocked sulfonic acid catalysts made from known processes. Toxicity testing is very expensive and is thus detrimental to the development of improved curing catalysts, since catalysts are generally used in small quantities and the expense for such testing is not justifiable.

It is, therefore, an objection of the present invention to develop curing catalysts that are polymeric with molecular weights of about 1000 and higher.

It is another objective of the present invention to develop polymeric curing catalysts that are storage stable.

Another objective of the present invention is to provide one package stable resin coating systems containing the polymeric curing catalysts which can used in electrostatic spray applications.

It is a further objective of the present invention to develop polymeric curing catalysts containing resin compositions that are storage stable and and can be used to provide cured thermosetting coatings which are superior in hardness, impact resistance, resistivity, with improved adhesion, blister resistance, salt spray characteristics and flexibility.

SUMMARY OF THE INVENTION

The invention is directed to a novel isocyanate modified blocked sulfonic acid catalyst useful for the crosslinking of polymers with hydroxyl, carboxyl and amide functional groups using an amino-formaldehyde resin, such as HMMA as a crosslinking agent and processes for preparation thereof and resin compositions containing the same. The isocyanate modified blocked sulfonic acid ester catalyst has the following structural formula:

$$R^1 {\Large[} \begin{matrix} O \\ \| \\ S-O-A \\ \| \\ O \end{matrix} \begin{matrix} O \\ \| \\ O-C-NH-R^3 \\ | \\ X \end{matrix} {\Large]}_n R^2$$

wherein:

$R^1$ is monovalent or divalent $C_{1-18}$ alkyl, $C_{1-18}$ alkylene, or $C_{1-18}$ mono- or di- alkyl substituted phenyl or naphthyl, optionally substituted with 1 to 2 sulfonic acid groups:

$R^2$ is H, mono or polyvalent $C_{1-18}$ alkyl, bisphenol A or bisphenol F, optionally substituted with a glycidyl or glycidyl derived moiety, such as $$-CH_2-\underset{\underset{OH}{|}}{CH}-CH_2-;$$

$R^3$ is $C_{1-18}$ alkyl, alkenyl, cycloalkyl, aryl or a polymeric moiety, optionally containing an ester, an ether or isocyanate functional or isocyanate derived group;

A is a multivalent linking group moiety derived from the ring opening reaction of an epoxy group with the following structure:

$$-CH-\underset{\underset{R^6}{|}}{\overset{\overset{R^4}{|}}{C}}-,$$
$$R^5$$

wherein $R^4$ is H or $-CH_2-$; $R^5$ and $R^6$ may be the same or different and each of $R^5$ and $R^6$ is H, $C_1-C_{12}$ alkyl or $R^4$ and $R^5$ together form a $C_6-C_{12}$ cycloalkyl;

n is 1-10 wherein if n is greater than 1, at least one of $R^1$, $R^2$ or $R^3$ is at least difunctional;

X is optional, and may be carboxy or oxy; and the molecular weight of the catalyst is at least about 1000.

The polymeric blocked sulfonic acid catalyst may be prepared by:

1. Reacting a $C_{1-18}$ alkyl, alkylenyl, phenyl or naphthyl mono-, di- or tri- sulfonic acid with a mono-, di- or polyepoxide, in a molar equivalent of epoxy to sulfonic acid group of 1:1 to 2:1, preferably 1.1:1 to 1.6:1, at a temperature in the range of about 0° C. to about 100° C., preferably room temperature to about 70° C., most preferably about 40° C. to 50° C. The reaction can be conducted without any solvents or in a anhydrous solvent, preferably an aprotic solvent. A small amount of a protic solvent can be tolerated; however, no water can be present. The resulting sulfonic acid ester is then reacted with a mono-, di- or poly- isocyanate at molar equivalents of OCN:OH of at least 1:1, preferably 1:1 to 1.5:1, at a temperature of about room temperature to 70° C., preferably room temperature to about 50° C. The reaction scheme as follows:

$$R^1SO_3H + CH_2\overset{O}{\overset{/\ \backslash}{-\!-\!-\!-}}CH-CH_2-X-R^2 \longrightarrow \qquad A.$$

$$R^1SO_3CH_2-\underset{\underset{OH}{|}}{CH}-CH_2-X-R^2$$

$$R^1SO_3-CH_2-\underset{\underset{OH}{|}}{CH}-CH_2-X-R^2 + OCN-R^3 \longrightarrow \qquad B.$$

$$R^1-SO_3-CH_2-\underset{\underset{O-C-NH-R^3}{\overset{\overset{O}{\|}}{|}}}{CH}-CH_2-X-R^2;$$

In step B a catalyst known for the reaction of isocyanates and hydroxyl compounds, such as a tin or zinc compound or a tertiary amine may be used.

2. Reacting a sulfonyl chloride with a diol in the presence of an acid scavenger, such as, tertiary amines, pyridines, alkaline metal bases including NaOH, KOH, NaOCH$_3$, then reacting the resulting sulfonic acid ester with a monomeric or polymeric isocyanate according to the following reaction scheme:

$$R^1SO_2Cl + HO-\underset{\underset{OH}{|}}{A}-X-R^2 \longrightarrow R^1SO_3-\underset{\underset{OH}{|}}{A}-X-R^2 + HCl \qquad A.$$

$$R^1SO_3-\underset{\underset{OH}{|}}{A}-X-R^2 + OCN-R^3 \longrightarrow \qquad B.$$

$$R^1SO_3-\underset{\underset{O-C-NH-R_3}{\overset{\overset{O}{\|}}{|}}}{A}-X-R^2$$

Both steps A and B of the reaction is conducted at a temperature in the range of room temperature to about 50° C. in the presence of an anhydrous, hydroxyl free and anprotic solvent such as xylene, toluene, mineral spirits and the like.

3. Reacting a polyol with an isocyanate and then reacting the product with sulfonyl chloride, reversing the order of addition of the reactants of reaction 2.

DETAILED DESCRIPTION OF THE INVENTION

The invention is directed to a novel isocyanate modified epoxy blocked sulfonic acid ester catalyst useful for the crosslinking of polymers having hydroxyl, carboxyl or amide functional groups with an amino-formaldehyde resin, such as HMMA and processes for preparation thereof and resin compositions containing the same. The isocyanate modified blocked epoxy sulfonic acid ester catalyst has the following structural formula:

$$R^1 {\Large[} \begin{matrix} O \\ \| \\ S-O-A \\ \| \\ O \end{matrix} \begin{matrix} O \\ \| \\ O-C-NH-R^3 \\ | \\ X \end{matrix} {\Large]}_n R^2$$

wherein:

$R^1$ is monovalent or divalent $C_{1-18}$ alkyl, alkylene or $C_{1-18}$ mono or dialkyl substituted phenyl or naphthyl, optionally substituted with sulfonic acid groups;

$R^2$ is H, mono or polyvalent $C_{1-18}$ alkyl, bisphenol A or bisphenol F, optionally substituted with a glycidyl or glycidyl derived moiety, such as $$-CH_2-\underset{\underset{OH}{|}}{CH}-CH_2-,$$

$R^3$ is a $C_{1-18}$ alkyl, alkenyl, cycloalkyl, aryl or a polymeric moiety, optionally containing ester, ether or isocyanate functional or isocyanate derived group;

A is a multivalent linking moiety derived from the ring opening reaction of an epoxy group having the following structure:

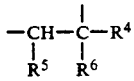

wherein $R^4$ is H or —$CH_2$—; $R^5$ and $R^6$ may be the same or different and each of $R^5$ and $R^6$ is H, $C_1$-$C_{12}$ alkyl or $R^5$ and $R^6$ together form a $C_6$-$C_{12}$ cycloalkyl;

n is 1-10 wherein if n is greater than 1, at least one of $R^1$, $R^2$ or $R^3$ is at least difunctional;

X is optional, and may be carboxy or oxy; and the molecular weight is at least about 1000.

The isocyanate modified blocked sulfonic acid catalysts may be prepared as follows:

1. Reacting a sulfonic acid with a mono, di or polyepoxide and then, reacting the resulting beta-hydroxyalkyl sulfonic acid ester with a mono-, di- or poly- isocyanate according to the following reaction scheme:

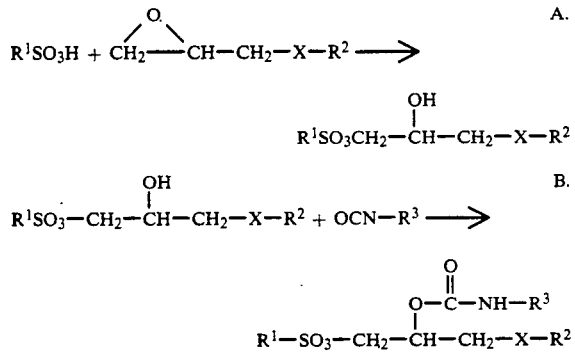

Step A may be conducted with or without a solvent. When a solvent is used, it is preferably a non-aqueous aprotic solvent, even though a small amount of a protic solvent can be tolerated. Examples of solvents which are useful include aromatic and nonaromatic hydrocarbons, ethers, ketones, esters and the like. These include toluene, xylenes, ethylbenzene, methylisobutyl ketone, acetone, ethyl acetate, butylacetate, methylethyl ether and the like. The amount of epoxy to sulfonic acid should be in a molar equivalent ratio of about 1:1 to 2:1, preferably about 1.1:1 to 1.6:1. The reaction is carried out at a temperature in the range of about 0° C. to 100° C., preferably room temperature to about 70° C. In step B, the reaction is carried out at a temperature of about room temperature to about 70° C., preferably room temperature to about 50° C. Any solvent if used is similar to that used in step A. Also, a metal catalyst, such as tin or zinc compounds or a tertiary amines, e.g. dibutyl tin dilaurate, zinc naphthanate, zinc octoate may be used in the reaction of step B.

Where the isocyanate is di- or poly- functional, the unreacted isocyanate groups of the catalyst can be utilized to react with the hydroxyl groups of the resin resulting in the polymeric catalyst being grafted to the backbone of the resin.

2. Reacting sulfonyl chloride with a polyol in the presence of an acid scavenger, such as, tertiary amines, pyridines, alkaline metal bases including NaOH, KOH $NaOCH_3$, and reacting the resulting sulfonic acid ester with a monomeric or polymer isocyanate according to the following reaction scheme:

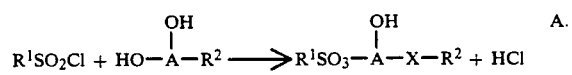

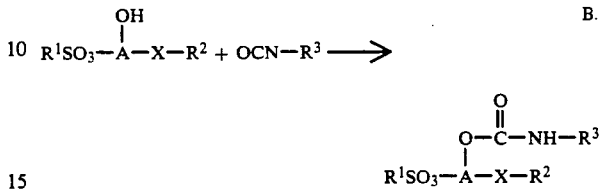

Both steps A and B of the reaction are carried out in an anhydrous, non-hydroxy and aprotic medium at a temperature in the range of room temperature to about 50° C. The anhydrous, non-hydroxy, and aprotic solvents include aromatic and non-aromatic hydrocarbons such as toluene, xylene, mineral spirits and the like.

3. Reacting a polyol with an isocyanate and then with sulfonyl chloride under the same conditions as reaction 2 above, but reversing the order of addition of the reactants.

The sulfonic acids that are suitable for this invention include mono- and di- sulfonic acids such as methane sulfonic acid, toluene sulfonic acid, alkyl naphthyl sulfonic acid, dialkylnaphthyl sulfonic acid, dialkyl naphthalene disulfonic acid, and the like.

Epoxy resins suitable for making the catalysts of the invention include diglycidyl ethers of bisphenol A and bisphenol F, diglycidyl ethers of polypropylene glycol, the mono glycidyl ethers of $C_1$ to $C_{18}$ alcohols, the glycidyl ester of $C_1$ to $C_{18}$ carboxylic acids, $C_2$ to $C_{18}$ alpha-olefin epoxides, isobutylene epoxides with a molecular weight of between about 350 to 2000, cycloaliphatic epoxy resins such as derived from the peracid epoxidation of cycloaliphatic compounds. Example of such cycloaliphatic epoxy resins are 3,4-epoxycyclohexylmethyl-3,4-epoxy-cyclohexane carboxylate, vinyl cyclohexane dioxide, 2-(3,4-epoxycyclohexyl-5,5-spiro-3,4-epoxy) cyclohexane-metadioxane, bis (3,4-epoxycyclohexyl) adipate.

Suitable isocyanates include 1,6-hexane diisocyanate, trimethyl hexane diisocyanate, isophorone diisocyanate, toluene diisocyanate, methylene dianiline derived products, such as, diphenylmethane-4,4′-diisocyanate, bis(4-isocyanatocyclohexyl) methane or tetramethylxylene diisocyanate, polyesters or polyethers terminated with an isocyanate group such as the reaction product of one mole of a polypropylene glycol with two moles of isophorone diisocyanate, or the reaction product of a polyester diol prepared from neopentyl glycol with adipic acid and an excess of isophorone diisocyanate.

Thermosetting resin compositions can be prepared to contain from 30 to 99 weight percent of a polymer resin having a hydroxyl, carboxyl, or amide functional group such as an acrylic, polyester, epoxy, alkyd, polyurethane or vinyl resins and 1 to 70 weight percent of an amino formaldehyde cross-linking agent selected form the group of $C_1$ to $C_8$ substituted alkoxymethyl amino compounds and from 0.003 to 0.3 meq/g preferably 0.02 to 0.08 meq/g of the catalyst of this invention per gram of the resin solids.

Amino crosslinking compounds useful in the present invention are typically the reaction products of an amino or amide compound such as melamine, benzoguanamine, urea, glycoluril, acrylamide, etc., with an aldehyde preferably formaldehyde and an alcohol or mixture of alcohols such as methanol, ethanol, propanol, isopropanol, isobutanol, n-butanol or other mono functional aliphatic alcohols of up to $C_8$ in chain length. A typical representative of this group of compounds is HMMA.

Solvents may optionally be included in the cure reaction. Solvents such as aliphatic or aromatic hydrocarbons, esters, ketones, glycol ethers, alcohols may be used. Typical examples include mineral spirit, xylene, toluene, ethylbenzene, ethylacetate, butylacetate, 2-ethoxyethylacetate, 2-methoxypropyl acetate, methylethylketone, methylisobutylketone, acetone, diisobutylketone, 2-methoxypropanol, 2-butoxyethanol, 2-ethoxyethoxyethanol, methanol, ethanol, propanol, butanol, and the like.

Suitable resins which may be crosslinked by using the catalysts of the present invention are polymers having a reactive hydroxyl, carboxyl or amide functional group, preferably two or more of these reactive groups. Typically the hydroxyl, carboxyl or amide content of the resin to be crosslinked corresponds to about 0.5 to 4 milliequivalents ("meq") preferably between 1 to 3 meq per gram of resin solids. These include:

A. Acrylic resins having either a carboxyl, hydroxyl or amide functional group such as obtained by copolymerization of the $C_1$ to $C_{18}$ alkyl ester of acrylic or methacrylic acid, styrene or substitutes styrene or acrylonitrile with functional monomers such as acrylic or methacrylic acid or the B-hydroxyalkylester of above acids. Typically the acrylic polymers have a molecular weight from about 2,000 to about 100,000. They are produced by conventional solution or bulk polymerization methods using free radical, or, if applicable, using ionic catalysts.

Copolymers of above acrylate monomers with the $C_1$ to $C_{18}$ ester or the hydroxyalkyl ester or half ester of maleic, fumaric or itaconic acid may also be used. Optionally, these resins can also contain other functional groups such as derived from the acetoacetoxyethyl methacrylate or acrylamide monomer. In addition, the acrylic resin can contain other non acrylate monomers such as vinylether or vinylacetate or vinylchloride. Acrylic copolymers, copolymers of butylacrylate/styrene/hydroxyalkylacrylate/acrylic acid with a molecular weight of 2500 to 8000, a hydroxyl number of between about 50 to 150 and an acid number of between 0 to 40; butylmethacrylate/hydroxyalkylacrylate copolymers with a hydroxyl number of between 50 to 200 or a meq of hydroxyl groups of about 1.0 to about 3.5 meq per gram of polymer solids; copolymers of ethyl, butyl, 2-ethylhexyl acrylate or methacrylate with styrene and a functional monomer such as acrylamide, hydroxyethyl or hydroxypropyl acrylate or methacrylate or optionally a carboxyl functional monomer such as acrylic or methacrylic acid or maleic acid.

Typical commercially available acrylic resins include ELVERON 100 (trademarked product of E.I. duPont de Nemours Inc.) ACRYLOID (trademarked product of Rohm & Haas Company) JOHNCRYL (trademarked product of Johnson was company).

B. Polyester or alkyd resins prepared by the esterification of diols, triols, tetraols or higher functional polyols with a mono-, di- or poly-basic acid. Examples for such acids are the naturally derived saturated and unsaturated $C_{12}$ to $C_{18}$ fatty acids, the dimers or higher oligomers of such fatty acids, the ortho, meta, or para phthalic acids, the aliphatic dicarboxylic acids such as succinic, glutaric, adipic, maleic, fumaric, sebasic, or dodecanoic acid, or higher functional acids such as trimellitic acid. The polyols are ethylene glycol, propylene glycol, 1,3-butylene glycol, 1,4-butylene glycol, 1,6-hexane diol, neopentyl glycol, diethylene glycol, dipropylene glycol, cyclohexane-dimethanol, glycerine, trimethylol ethane or propane pentaerythritol etc. The polyester or alkyd resin useful in the present invention usually have a molecular weight of 400 to about 15,000, and a hydroxyl or carboxyl functionality of between about 0.2 to about 6 meq/g of resin solids, preferably between about 1 to 5 meq/g. Polyester resins derived from neopentylglycol, trimethylol, trimethylol propane, adipic and isophthalic acid with a molecular weight of between about 400 to 3000, a hydroxyl number of 340 to 10 or about 0.2 to 6 meq/g of resin solids, preferably 1 to 5 have been found to be applicable. Alkyd resins prepared from a non drying oil such as coconut oil with a triol such as glycerine and phthalic anhydride as a dibasic acid have also been found to be applicable. The variety of polyester resins and alkyds commercially available is numerous and there is no restriction on their compositions as long as they have either hydroxyl or carboxyl functional groups.

Typical polyester resins are available commercially. These include FLEXOREZ 55-56 (trademarked product of Witco) CYPLEX 1546 (trademarked product of Cyanamid Corporation) AROPLAZ 6025 (trademarked product from Spencer Kellogg) and K-FLEX 188 and 148 (trade marked products of King Industries).

C. Low to higher molecular weight epoxy resins derived from bisphenol A bisphenol F or epichlorohydrin. Such resins have a molecular weight of about 800 to 10,000 preferably between about 1,000 to 5,000 and have, besides epoxy groups, hydroxyl functional groups. Examples of such resins include EPON from Shell Chemical Company, DER from Dow Chemical Corporation, Araldite from Ciba-Geigy Corporation.

D. Hydroxyl functional group containing polyesterurethane polymers such as the reaction products of a cyclohexane dimethanol- adipic acid polyester resin with isophorone diisocyanate.

E. Vinyl polymers such as copolymers of vinylacetate with vinylchloride with a hydroxyl functional monomer. Commerically available vinyl resins may include VACH, VROH, VYES (Union Carbide).

Paints and coating prepared with catalyst of the present invention have improved resistivity, making them more suitable for electrostatic spray applications.

The blocked sulfonic acid catalyst or the present invention has by itself superior storage stability when compared with a blocked sulfonic acid of the prior art, catalyst without isocyanate modification. Not only is the photo stability of the catalyst superior, stability studies at 50° C. also give a reduced rate of acid formation. It had been observed that the presence of unreacted beta-hydroxyalkyl groups in the epoxy blocked catalysts of the prior art catalyzes the decomposition of the sulfonic acid ester at storage temperatures of 50° C. Whereas, in the catalyst of the present invention, these hydroxyl groups are absent. As a result the stability at 50° C. of the catalysts of the present invention is much improved.

In commercial epoxy blocked catalysts of the prior art, the limitation in storage stability has long been a problem. In order to overcome the limited shelf life, the supplier of these catalysts have added an excess of an epoxy containing compound, to provide some improvement in storage stability because any decomposed sulfonic acid ester could react with the excess of epoxy resin. Unfortunately, this approach has its limitations, the presence of an excess epoxy resin during cure either inhibit or delay the reaction. In addition, depending on the age of the catalyst and the level of excess epoxy resin the coating formulation prepared with such a catalyst showed varying cure responses. Moreover, the decomposition of the epoxy blocked catalysts of the prior art is probably responsible for the increased discoloration of the catalyst solutions on storage.

The decomposition of the epoxy blocked catalyst of the prior art can also increase with the addition of hydroxyl functional solvents. In theory, the stability of the catalyst of the present invention is also substantially reduced in the presence of an alcohol. However, from a practical standpoint, this is not a problem. The catalyst of the present invention are prepared in an anhydrous hydroxyl free solvent to permit the reaction of the isocyanate with the beta-hydroxylalkyl groups of the sulfonic acid ester to form the catalyst of the present invention. Therefore, the formed catalyst is intrinsically alcohol free.

The catalyst of the present invention although very stable by itself for prolonged time periods will be activated in a paint or coating formulation in the presence of a hydroxyl functional polymer. Another advantage of the catalyst of the present invention is that, these catalysts are nonionic and are soluble in all conventional polar and non polar solvents. Whereas, amine blocked sulfonic acids of the prior art have poor solubility in certain polar and non polar solvents and are generally soluble only in alcohols.

The above advantages are realized when the catalysts of the present invention are utilized to cure thermosetting polymers for paints and coating applications.

The following examples illustrate the invention. However, it is to be understood that the examples are not to be used to limit the scope of the invention.

EXAMPLE 1

Catalyst A 150 parts by weight of dodecylbenzene sulfonic acid, DDBSA, (0.5 mol) were charged into suitable reactor diluted with 150 parts of xylene and slowly, under cooling, 200 parts by weight of a glycidyl ester of a highly branched $C_{10}$ neodecanoic acid, NDA, (0.8 mol) were added. The reaction temperature was kept at about 40°-50° C. The reaction was held at 50° C. for about 8-10 hours, or until the acid number is <1.0. To this hydroxy functional sulfonic ester, 60 parts by weight of isophorone diisocyanate (0.27 meq of IPDI or 0.54 meq of isocyanate) were added. The reaction was catalyzed with about 0.1 part by weight of dibutyltin dilaurate. The reaction was exothermic and was cooled to about 60° C. The reaction was followed by infrared spectroscopy, showing the disappearance of the isocyanate, NCO, group. After holding the reaction mixture at 50°-60° C. for 6-7 hours most of the NCO groups have disappeared.

The reaction product had a solids content of 73%; a viscosity at 25° C. of 32 cps; an active sulfonic content of 27%; Gardner color of 2; and a molecular weight of 1320. The compound formed has the following structural formula:

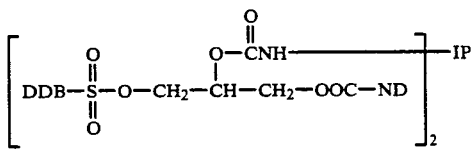

Key:
DDB = 4-dodecylbenzene
ND = neodecane
IP = isophorone

EXAMPLE 2

Comparative Example Catalyst B 150 parts by weight of DDBSA (0.5 mol) were charged into a suitable reactor diluted with 150 parts of xylene and, slowly under cooling, 200 parts by weight of a glycidyl ester of a highly branched $C_{10}$ NDA (0.8 mol) were added. The reaction temperature was kept at about 40°-50° C. The reaction was held at 50° C. for about 8-10 hours, or until the acid number is <1.0. The reaction product was the sulfonic ester of the glycidyl ester. The reaction was also followed by IR spectroscopy, showing the disappearance of the epoxy groups and the formation of the beta-hydroxy alkyl groups.

The final product had a solids content of 70%, a viscosity at 25° C. of 22 cps. The active acid content was 30%. The molecular weight of the compound is 550.

EXAMPLE 3

A commercially available polyester resin (69.31 wt. %) was blended with a hexamethoxymethylmelamine resin (29.70 wt. %). The mixture was catalyzed with 0.99 wt. % 0.03 meq/g calculated on the basis of DDBSA, of Catalyst A. A comparative formulation was catalyzed with 0.99 wt. % (0.03 meq/g) of Catalyst B. In addition, a comparative study was conducted with 0.99 wt. % (0.03 meq/g) of Catalyst C, DDBSA neutralized with diisopropanol amine. Curing was carried out at 120° C. and 150° C. for 20 minutes on iron phosphate pretreated steel substrate. The results of this study are shown on Table I.

TABLE I

| | Catalysts | | | | | |
| | A | | B | | C | |
| | Curing Temperature | | | | | |
| Characteristics | 120° C. | 150° C. | 120° C. | 150° C. | 120° C. | 150° C. |
| Hardness (Knoop 25 g) | 9.4 | 12.4 | 9.1 | 12.0 | 9.6 | 13.3 |
| Impact Resist. | | | | | | |
| (Reverse lb) | >160 | 80–90 | >160 | 10–20 | >160 | 60–70 |
| (Front lb) | >160 | >160 | 140–150 | 60–70 | >160 | 60–70 |
| Adhesion | 0 | 0 | 0 | 0 | 0 | 0 |

TABLE I-continued

| | Catalysts | | | | | |
|---|---|---|---|---|---|---|
| | A | | B | | C | |
| | Curing Temperature | | | | | |
| Characteristics | 120° C. | 150° C. | 120° C. | 150° C. | 120° C. | 150° C. |
| (Crosshatch %) Humidity Resist. (60° C./168 hrs) | — | 8MD* | — | 8D** | — | 8D** |

*8D = dense, 0.5 mm id blisters
**bMD = medium dense, 0.5 mm id. blisters

Based on the above test data, the film cured with catalyst A is more flexible with improved impact resistance and was more resistant to humidity.

Additionally, the films formed using catalysts A and B have good electrostatic spray characteristics.

EXAMPLE 4

Catalysts A, B and a commercial catalyst dimethyloxazolidine neutralized DDBSA; were used to cure an acrylic acid crosslinked with HMMA. The resin composition and results are shown in Table II.

TABLE II

| | Grind Formulation | | |
|---|---|---|---|
| | #1 | #2 | #3 |
| TiO₂ | 80.36 | 80.36 | 80.36 |
| Elveron 100ª | 38.94 | 38.97 | 38.97 |
| n-Butyl acetate | 1.23 | 1.23 | 1.23 |
| Xylene | 1.23 | 1.23 | 1.23 |
| Letdown | 75.86 | 75.86 | 75.86 |
| Elveron 100 | 34.44 | 34.44 | 34.44 |
| Cymel 1133ᶜ | 21.27 | 21.27 | 21.27 |
| Xylene | 10.92 | 10.92 | 10.92 |
| Catalyst A | 6.42 | | |
| Catalyst B | | 5.73 | |
| Catalystᵇ | | | 6.88 |

Test results
Baking schedule 30 min 120° C.
Film thickness 0.8 mil

| Formulation # | Hardness Knoop Pencil | Impact Rev/Front inch · lbs | MEK double rubs | SALT SPRAY 120 HRS |
|---|---|---|---|---|
| 1 | 18.4 4H-5H | <5/30-40 | >100 | 4D*, 6 mm** |
| 2 | 18.0 4H-5H | <5/30-40 | >100 | 4D, 5 mm |
| 3 | 17.2 4H-5H | <5/30/40 | >100 | 4D, 14 mm |

ªCommercial high solids acrylic resin from Dupont.
ᵇCommercial dimethyloxazolidine neutralized DDBSA catalyst. Active acid 25%.
ᶜCommercial mixed ether methylated/butylated melamine formaldehyde resin.
*The numerical value indicates the average size of the blisters, with 1 being 8 mm and 10 being 0 mm, i.e., no blisters.
**Creepage in mm from scribe line.

The films, with the exception of the resin composition formulation #1 utilizing catalyst A, had a tendency to crater and required 0.2% of an acrylic flow control agent.

EXAMPLE 5

Prior Art Propoxy Blocked Catalyst

Example 2 is repeated in all details with the exception that the glycidyl ester of the highly branched C₁₀ neodecanoic acid was replaced with an equal molar amount of propylene oxide (46.4 part by weight). The resulting product after an aging time of 24 hours had a residual acid number of about 3.6. After addition of 7 parts by weight of propylene oxide and an additional 4 hours of aging at 50° C., the acid number of the product was 0.3. The meq/g of the catalyst used was 1.315.

EXAMPLE 6

Isocyanate Modified Propoxy Blocked Catalyst 455 parts by weight of the reaction product of Example 5 (0.625 mol) are reacted with 72 parts by weight of isophorone diisocyanate (0.65 NCO). About 0.05 parts of dibutyltin dilaurate was used as a catalyst. The reaction is conducted at 50° C. for 7 hours. After the holding period, IR spectroscopy was used to confirm the disappearance of the NCO groups. The meq/g of the catalyst used was 1.315.

The structural formula of the catalyst is:

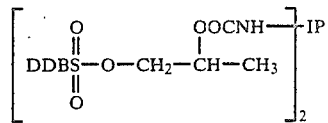

Key:
DDB = 4-dodecylbenzene
IPI = isophorone

EXAMPLE 7

Butoxy Blocked Catalyst 450 parts by weight of a 60% solution of dinonylnaphthalene disulfonic acid (DNNDSA), (0.5 mol sulfonic acid) in n-butanol was reacted with 282 parts by weight of butylene oxide (3.9 mol) at 40°-50° C. to an acid number of <1.0. Excess butylene oxide was used as a water scavenger in the DNNDSA. The resulting product had an active acid content 1.367 milliequivalent (meq) per gram calculated as the sulfonic acid ester. The viscosity was 62 cps at 25° C. at a weight solids content of 53.3%.

EXAMPLE 8

Isocyanate Modified Butoxy Blocked Catalyst 18 349 parts by weight of the sulfonic acid ester of Example 7 (0.2384 mol of DNNDSA) was reacted with 80 parts by weight of isophorone diisocyanate (0.72 mol of NCO). About 0.05 parts by weight of dibutyltin dilaurate was used as a catalyst. The reaction is run at 50° C. for 3 hours. At the end of the reaction as indicated by IR analysis the sample was diluted with 50 parts by weight of xylene. The resulting product has a solids content of about 70.2%, an acid content of 0.998 meq/g calculated as the sulfonic ester. The viscosity of the product was 2150 cps at 25° C.

The structural formular of the catalyst is as follows:

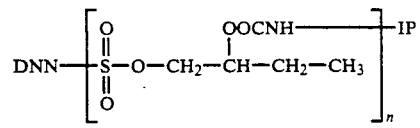

Key:
DNN = dinonylnaphthalene
ID = isophorone
n = 3 to 5

EXAMPLE 9

Epoxy Blocked Catalyst 162.5 parts by weight of dodecylbenzene sulfonic acid and 325 parts per weight of a diglycidyl ether of polypropylene glycol with an epoxy equivalent weight of 162.5 were reacted at 50° C. for 8 hours in 100 parts per weight of toluene as a solvent. The resulting product had a solids content of 83% and an active acid content of 0.848 meq/g. The residual acid number was <1.0.

EXAMPLE 10

Isocyanate Modified Epoxy Blocked Catalyst 301.5 parts per weight of reaction mixture of Example 9 were blended with 57 parts per weight of isophorone diisocyanate and 105 parts per weight of toluene and 0.3 parts per weight of dibutyltin dilaurate. After 16 hours at room temperature 19 parts per weight of isopropanol are charged to remove any residual NCO groups. The resulting product has a solids content of 67.6% and an active acid content of 0.530 meq/g.

The structural formula of the resulting product is:

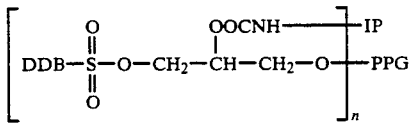

Key:
PPG = polypropylene glycol
DDB = 4 dodecylbenzene
IPI = isophorone
n = 3 to 5

EXAMPLE 11

Samples of catalysts of Examples 1, 2, 5, 6, 7 and 8 were exposed in a vial for 3 months to sunlight. A sample of catalyst of Example 7 was also blended with a small amount of dibutyltin dilaurate equivalent to the amount of catalyst used in Example 8, and exposed to light.

During the exposure the comparative pairs of catalysts are checked for color changes. After about 1 month samples 1, 6 and 8 showed reduction in color. Samples of catalyst 2, 5 and 7 on the other hand darkened considerably. Because a possible effect of the tin catalyst on the light stability was suspected a catalyst prepared according to Example 7 was doped with an appropriate level of tin catalyst. This sample showed discoloration about equal to Example 7. Additional exposure to light for another month continued the trend of bleaching of the isocyanate modified catalyst of the present invention on light. Samples stored in the dark showed a similar behavior, albeit at much slower rates.

Determination of the acid number of catalyst A and B after 7 month in full sun light showed an acid number of <1 and 30 respectively.

The Gardner color of catalyst A after the aging period was about 1; whereas for catalyst B it was 10.

The results indicate that catalyst B has degraded considerably. Whereas, catalyst A is stable.

EXAMPLE 12

102 parts by weight of a narrow molecular weight, commercially available polyester resin with an average molecular weight of 450 and a hydroxyl number of 235 is blended with 42.8 parts by weight of a hexamethoxymethylmelamine crosslinking agent. The formulation is diluted with 30 parts by weight of toluene. 0.05 parts by weight of a silicone surfactant was used as an anti-crater agent. The results of this evaluation are shown in Tables IIIa and b.

TABLE III

POLYMERIC FILM PROPERTIES ON BONDERITE 1000 COLD ROLLED STEEL

| | CATALYST USED | | | | | | |
|---|---|---|---|---|---|---|---|
| | Example 5 | Example 6 | Example 7 | Example 8 | Example 9 | Example 10 | COMPARATIVE[a] CATALYST |
| Active Acid % | 42.9 | 37.04 | 36.9 | 26.9 | 27.7 | 17.3 | 25.0 |
| Acid, meq/g | 1.315 | 1.135 | 1.369 | 0.998 | 0.848 | 0.53 | 0.766 |
| Solids, % | 57.1 | 50.7 | 53.3 | 70.2 | 83.0 | 67.6 | 70.0 |
| MW | 384 | 991 | 655 | 1532 | 966 | 2154 | 305 |
| Solvent | | | | | TOLUENE | TOLUENE | ISOPROPANOL |
| Film Properties | | | | | | | |
| Knoop Hardness 20 min 120° C./150° C. | <1.0/9.3 | 8.2/11.2 | 2.2/9.7 | 6.2/10.4 | 0/6.9 | 6.6/10.4 | 10.4/12.4 |
| Impact Resistance in · lb. | | | | | | | |
| Reverse 120° C./150° C. | >160/>160 | >160/120 | >160/>160 | >160/>160 | —/>160 | >160/>160 | 100/20 |
| Direct 120° C./150° C. | >160/>160 | >160/140 | >160/>160 | >160/>160 | —/>160 | >160/>160 | >160/120 |
| Cross hatch adhesion % | * | 0 | 96 | 84 | ** | 0 | 0 |
| Saltspray hours | — | 144 | 144 | 144 | | 144 | 72 |
| creep cm | — | 1.1 | 0.6 | 0.6 | | 1.3 | 1.7 |
| adhesion % | — | 0 | 0 | 100 | | 0 | 0 |
| Humidity hours | — | 168 | 168 | 168 | | 144 | 72 |

TABLE III-continued

POLYMERIC FILM PROPERTIES ON
BONDERITE 1000 COLD ROLLED STEEL

|  | CATALYST USED | | | | | | |
|---|---|---|---|---|---|---|---|
|  | Example 5 | Example 6 | Example 7 | Example 8 | Example 9 | Example 10 | COMPAR-ATIVE[a] CATALYST |
| Blistering | — | 4 D | 8 F | 10 | | 7 D | 6 D |

[a]Comparative catalyst Dodecylbenzene sulfonic acid blocked with dimethyloxazolidine.
*All corrsion tests were conducted on 20 min. and 120° C. cured panel. Example 5 was not sufficiently cured for testing.
**Not cured at 20 min 120° C.

The data at the lower cure temperature show higher hardness development when using an isocyanate modified epoxy blocked catalyst of the present invention when compared to a catalyst prepared from a sulfonic acid and an epoxide. The data also show superior humidity resistance.

The value for active acid indicates the amount of dodecylbenzene or dinonylnaphthalene sulfonic acid (expressed as free acid) which is available for catalysis. The amount is expressed in weight percent. Solids % is the weight percent of catalyst in the formulation in blocked form.

EXAMPLE 13

Catalyst A of Example 1 was used in a range of different resin systems. A commercially available acrylic resin (AT-400) with a hydroxyl number of 80 and an acid number of 30 (Rohm & Haas) was crosslinked with a commercially available hexamethoxymethylmelamine resin (Cymel 303, C303, American Cyanamid Comp.). In the second formulation the acrylic melamine resin was modified with a commercially available low molecular weight polyester resin (K-FLEX® 188, K188, King Industries). The third formulation utilizes only the polyester resin in combination with a mixed ether methylated butylated hexamethylol malamine resin (Cymel 1130, C1130 from American Cyanamid Comp.).

The formulations were catalyzed with 0.03 meq/g of Catalyst A of Example 1 and a comparative amine neutralized dodecylbenzene sulfonic acid. The results of the evaluation are shown in Table IV.

TABLE IV

Cure Schedule: 20 min 125° C.
Film Thickness 1.0 mil

| Description | Catalyst | Hardness Knoop 25 g | Impact resist. IN. LBS/PASS REV. | Front |
|---|---|---|---|---|
| POLYMERIC FILM PROPERTIES ON BONDERITE 1000 COLD ROLLED STEEL | | | | |
| ACRYLIC AT-400/C303 80/20 | A | 7.75 | 40 | 60 |
| ACRYLIC AT-400/K188/C303 37.5/37.5/25 | A | 9.32 | 100 | 80 |
| POLYEST. K188/C1130 70/30 | A | 8.67 | 140 | 80 |
| ACRYLIC AT-400/C303 80/20 | COMP. | 9.49 | 60 | 40 |
| ACRYLIC AT-400/K188/C303 37.5/37.5/25 | COMP. | 2.24 | 160 | 160 |
| POLYEST. K188/C1130 70/30 | COMP. | 8.23 | 0 | 0 |
| FILM PROPERTIES ON CLEAN ALUMINUM | | | | |
| ACRYLIC AT-400/C303 80/20 | A. | 9.40 | 10 | 10 |
| ACRYLIC AT-400/K188/C303 37.5/37.5/25 | A | 9.75 | 10 | 10 |
| POLYEST. K188/C1130 70/30 | A | 8.37 | 40 | 20 |
| ACRYLIC AT-400/C303 80/20 | COMP. | 9.53 | 8 | 10 |
| ACRYLIC AT-400/K188/C303 37.5/37.5/25 | COMP. | 10.00 | 0 | 10 |
| POLYEST. K188/C1130 70/30 | COMP. | 8.72 | 0 | 10 |

EXAMPLE 14

The formulations utilizing the catalysts in Examples 3 and 12 are aged at room temperature and elevated temperatures, and the viscosity is measured during the aging process. The results of the evaluation are shown in Table V.

TABLE V

STABILITY OF CATALYZED FORMULATIONS
Viscosity IN CPS

| | Catalyst Example | | | | | | | |
|---|---|---|---|---|---|---|---|---|
| | 1 | 2 | 5 | 6 | 7 | 8 | 9 | 10 |
| 0 DAYS RT | 287 | 377 | 257 | 294 | 259 | 328 | 301 | 327 |
| 10 DAYS RT | 356 | 822 | 319 | 578 | 336 | 443 | 327 | 434 |
| 3 DAYS 50° C. | 9600 | 11400 | 463 | 4680 | 650 | 1900 | 372 | 2320 |
| 5 DAYS 50° C. | | GEL | | | | | | |
| 7 DAYS 50° C. | 21500 | | | | | | 377 | 6300 |
| 10 DAYS 50° C. | GEL | | 2120 | 15800 | 5919 | 23400 | 417 | 7870 |

This table shows that the catalyst of example 5, 7, and 9 in a coating formulation results in superior stability as shown by a smaller increase in viscosity. However, the catalyst do not cure at a temperature of 120° C. Whereas, the catalysts prepared according to the present invention 6, 8 and 10 are more reactive at a lower temperature of 120° C. even though a less stable coating is formed.

The is not completely surprising considering the apparent higher rate of decomposition at 120° C. A comparison of catalyst A and B at equal rate of cure shows that catalyst A gave a coating of superior stability over catalyst B.

EXAMPLE 15

The formulations of Example 12, utilizing Catalyst A of Example 1, were used to test several approaches to improve the storage stability. The results are shown in Table VI.

TABLE VI

STABILITY OF CATALYZED FORMULATIONS VISCOSITY IN CPS
Catalyst A 1 0.03 meq/g

| | | | | ADDITIVE % on binder | | | | |
|---|---|---|---|---|---|---|---|---|
| | NO | TEA | DIPA | BUTYLENE OXIDE | | | GLYCIDYL ESTER | |
| Time and Temp. | ADD. | 0.239 | 0.32 | 0.17 | 0.34 | 1.1 | 0.59 | 1.18 |
| 0 DAYS RT | 287 | 329 | 286 | 214 | 291 | 270 | 331 | 319 |
| 10 DAYS RT | 356 | 336 | 311 | 392 | 394 | 300 | 431 | 417 |
| 3 DAYS 50° C. | 9600 | 359 | 412 | 7410 | 2050 | 350 | 11800 | 11000 |
| 5 DAYS 50° C. | | 349 | 479 | 16100 | 3590 | 405 | 26700 | 27700 |
| 7 DAYS 50° C. | 21500 | 356 | 494 | GEL | 5590 | 494 | GEL | GEL |
| 10 DAYS 50° C. | GEL | 372 | 642 | | 21000 | 542 | | |

TEA = triethylamine
DIPA = diisopropanol amine

The above data shows that the catalysts of the present invention can be stabilized by addition of small amounts of TEA, DIPA, butylene oxide.

Example 15 demonstrates that the increase curing rate of the catalysts of the present invention can be stabilized by using either a small level of amine or an epoxide. The same improvement in stability with amine addition or with epoxy addition could be seen with the epoxy blocked sulfonic acid catalysts of prior art, however these systems lack the cure response of the catalyst of the present invention.

EXAMPLE 16

(Comparative)

The formulation of Example 12 utilizing the comparative dimethylozazolidine amine blocked dodecylbenzene sulfonic acid catalyst was aged at room temperature and 50° C. The results are shown in Table VII.

TABLE VII

| DDBSA Amine blocked catalyst | STABILITY VISCOSITY IN CPS |
|---|---|
| 0 DAYS RT | 244 |
| 10 DAYS RT | 321 |
| 3 DAYS 50° C. | 422 |
| 7 DAYS 50° C. | 852 |
| 10 DAYS 50° C. | 1120 |

The amine blocked DDBSA catalyst, Catalyst C, as shown in example 3 is equivalent in cure response at the lower cure temperature of 120° C. The stability of the paint containing catalyst C is superior to the catalyst of the present invention in the absence of any stabilizer. However, as seen in Example 15, the addition of a small level of either an amine or butylene oxide can provide superior stability as compared to Example 16, an amine stabilized catalyst.

Addition of amine can also improve the stability of the comparative amine blocked catalyst, but will not improve the film properties of coatings prepared with this catalyst. Addition of butylene oxide to the amine blocked catalyst leads to the reaction of the butylene oxide with the amine and of inhibition cure.

I claim:

1. An isocyanate modified epoxy blocked sulfonic acid catalyst having the structural formula:

$$R^1 \left[ \begin{array}{c} O \\ \parallel \\ S-O-A \\ \parallel \\ O \end{array} \begin{array}{c} O-C-NH-R^3 \\ | \\ X \end{array} R^2 \right]_n$$

wherein:
R$^1$ is monovalent or divalent C$_{1-18}$ alkyl, C$_{1-18}$ alkylene, or C$_{1-18}$ mono- or di- alkyl substituted phenyl or naphthyl, optionally substituted with 1 to 2 sulfonic acid groups;
R$^2$ is H, mono or polyvalent C$_{1-18}$ alkyl, bisphenol A or bisphenol F, optionally substituted with a glycidyl or glycidyl derived moiety, such as $$-CH_2-\overset{OH}{\underset{|}{CH}}-CH_2-;$$

R$^3$ is C$_{1-18}$ alkyl, alkenyl, cycloalkyl, aryl or a polymeric moiety, optionally containing an ester, an ether or isocyanate functional or isocyanate derived group;
A is a multivalent linking group moiety derived from the ring opening reaction of an epoxy group with the following structure:

$$-\underset{R^5}{\overset{|}{CH}}-\underset{R^6}{\overset{|}{C}}-R^4,$$

wherein R$^4$ is H or —CH$_2$— and R$^5$ and R$^6$ may be the same or different and each of R$^5$ and R$^6$ is H, C$_1$–C$_{12}$ alkyl or R$^5$ and R$^6$ together form a C$_6$–C$_{12}$ cycloalkyl;
n i 2–10 and at least one of R$^1$, R$^2$ or R$^3$ is at least difunctional; and
X is optional, and may be carboxy or oxy; and the molecular weight of the catalyst is at least about 1000.

2. An isocyanate modified epoxy blocked sulfonic acid catalyst according to claim 1 wherein $R^1$ is $C_{1-18}$ alkyl, alkylbenzene, alkyl naphthyl, dialkyl naphthyl, dinonylnaphthalene sulfonate; A is

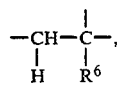

wherein $R^6$ is H, $C_1$-$C_4$ alkyl; $R^2$ is H, $C_{1-4}$ alkyl, bisphenol A or bisphenol F optionally substituted with glycidyl or

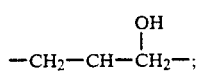

X is —O—, $R^3$ is $C_{6-12}$ alkyl isocyanato, isophorone isocyanato, tolulene isocyanato.

3. An isocyanate modified epoxy blocked sulfonic acid catalyst according to claim 2 wherein $R^1$ is dodecylbenzene.

4. An isocyanate modified epoxy blocked sulfonic acid catalyst according to claim 2 wherein $R^1$ is dinonylnaphthylene.

5. An isocyanate modified epoxy blocked sulfonic acid catalyst according to claim 2 wherein $R^1$ is dinonylnaphthylene sulfonato.

6. An isocyanate modified epoxy blocked sulfonic acid catalyst according to claim 3 wherein A is

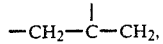

x is

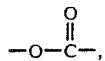

$R^2$ is neononyl, $R_3$ is isophoronyl isocyanato, and n is 2.

7. An isocyanate modified epoxy blocked sulfonic acid catalyst according to claim 3 wherein A is

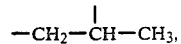

$R^3$ is isophoronyl isocyanato and n is 2.

8. An isocyanate modified epoxy blocked sulfonic acid catalyst according to claim 3 wherein $R^1$ is 4-dodecyl benzene, A is

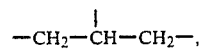

X is —O— and $R^2$ —$(CH_2-CH_2-CH_2-O)_p$—, wherein p is 2-5, $R^3$ is isophoronyl isocyanato and n is 2-5.

9. An isocyanate modified epoxy blocked sulfonic acid catalyst according to claim 3 wherein A is

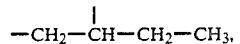

$R^3$ is isophoronyl isocyanato and n is 2.

* * * * *